(12) United States Patent
Liu et al.

(10) Patent No.: US 8,609,667 B2
(45) Date of Patent: Dec. 17, 2013

(54) E-TYPE PHENYL ACRYLIC ESTER COMPOUNDS CONTAINING SUBSTITUTED ANILINO PYRIMIDINE GROUP AND USES THEREOF

(75) Inventors: Changling Liu, Shenyang (CN); Huichao Li, Shenyang (CN); Hong Zhang, Shenyang (CN); Baoshan Chai, Shenyang (CN); Yanmei Luo, Shenyang (CN); Xiaomin He, Shenyang (CN); Guang Huang, Beijing (CN); Shaowu Liu, Beijing (CN); Baoxiang Sun, Beijing (CN)

(73) Assignees: Sinochem Corporation, Beijing (CN); Shenyang Research Institute of Chemical Industry Co., Ltd., Shenyang (CN)

( * ) Notice: Subject to any disclaimer, the term of this patent is extended or adjusted under 35 U.S.C. 154(b) by 98 days.

(21) Appl. No.: 13/265,379

(22) PCT Filed: Jun. 3, 2010

(86) PCT No.: PCT/CN2010/073484
§ 371 (c)(1),
(2), (4) Date: Oct. 20, 2011

(87) PCT Pub. No.: WO2010/139271
PCT Pub. Date: Dec. 9, 2010

(65) Prior Publication Data
US 2012/0035190 A1 Feb. 9, 2012

(30) Foreign Application Priority Data
Jun. 5, 2009 (CN) .......................... 2009 1 0084967

(51) Int. Cl.
*C07D 239/47* (2006.01)
*A01N 43/54* (2006.01)
(52) U.S. Cl.
USPC ..................... 514/258.1; 514/266.3; 514/272; 544/253; 544/287; 544/321

(58) Field of Classification Search
USPC ............ 544/253, 287, 321; 514/258.1, 266.3, 514/272
See application file for complete search history.

(56) References Cited

U.S. PATENT DOCUMENTS

| | | | |
|---|---|---|---|
| 6,114,342 A | 9/2000 | Oberdorf | |
| 8,383,640 B2 * | 2/2013 | Liu et al. | ....................... 514/272 |

FOREIGN PATENT DOCUMENTS

| | | | |
|---|---|---|---|
| CN | 101311170 A | | 11/2008 |
| WO | WO 2008/145052 | * | 12/2008 |

OTHER PUBLICATIONS

Chai et al., The discovery of SYP-10913 and SYP-11277 novel strobilurin acaricides, Pest Management Science, vol. 67, pp. 1141-1146 (Mar. 2011).*
International Search Report received in PCT/CN2010/073484, mailed Sep. 9, 2010. English translation provided.
Supplementary European Search Report received in EP 10782975, mailed Oct. 25, 2012.

* cited by examiner

*Primary Examiner* — Deepak Rao
(74) *Attorney, Agent, or Firm* — Dennis C. Rodgers, Esq.; Smith, Gambrell & Russell, LLP

(57) ABSTRACT

Disclosed is a kind of E-type phenyl acrylic ester compound containing substituted anilino pyrimidine group, which is shown by general structure formula I, wherein each substituent is defined as that in the description. The compounds of general formula I show high insecticidal and acaricidal activities to adults and nymphs of harmful insects and mites in agricultural, civil and zoic technical fields, especially to *Tetranychus cinnabarinus*, Tetranychidae, and the like. The said compounds show more excellent performance on inhibiting the incubation of eggs of harmful mites. The uses of the said compounds as insecticides and/or acaricides in agricultural and other fields also are disclosed.

5 Claims, No Drawings

E-TYPE PHENYL ACRYLIC ESTER COMPOUNDS CONTAINING SUBSTITUTED ANILINO PYRIMIDINE GROUP AND USES THEREOF

FIELD OF THE INVENTION

The invention relates to insecticide and acaricide in agricultural, civil and zoic technical fields. Specifically to a kind of E-type phenyl acrylic ester compounds containing substituted anilino pyrimidine group and uses thereof.

BACKGROUND OF THE INVENTION

Natural products, methoxyacrylate compounds, are known compounds with biological activity. Methoxyacrylate compounds as insecticides and acaricides were reported in the following literatures: EP242081, EP299694, EP335519, US2006235075, etc.

In addition, methoxyacrylate compounds containing pyrimidine moiety were also disclosed as insecticides, acaricides or fungicides:

The compounds used as insecticides having the following general formula were mentioned in U.S. Pat. No. 5,106,852:

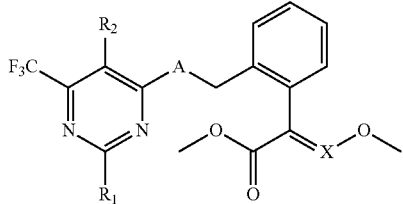

Wherein: $R_1$ is selected from alkyl, cycloalkyl, haloalkyl, alkoxy, alkylthio or substituted and unsubstituted aryl.

U.S. Pat. No. 5,378,711 related to the following compounds as insecticides:

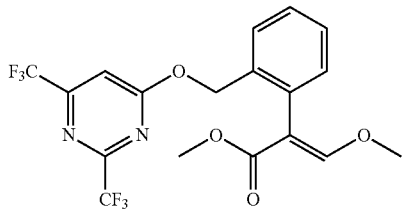 [SMILES: CO/C=C(/C(=O)OC)c1ccccc1COc1cc(C(F)(F)F)nc(C(F)(F)F)n1]

The compounds of the following general formula with acaricidal, fungicidal activity were disclosed in U.S. Pat. No. 5,935,965:

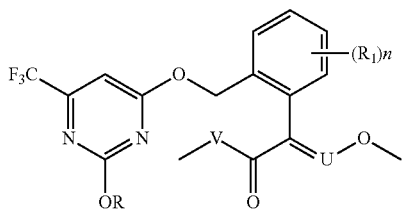

The compounds of the following general formula with insecticidal, fungicidal activity were reported in U.S. Pat. No. 6,114,342:

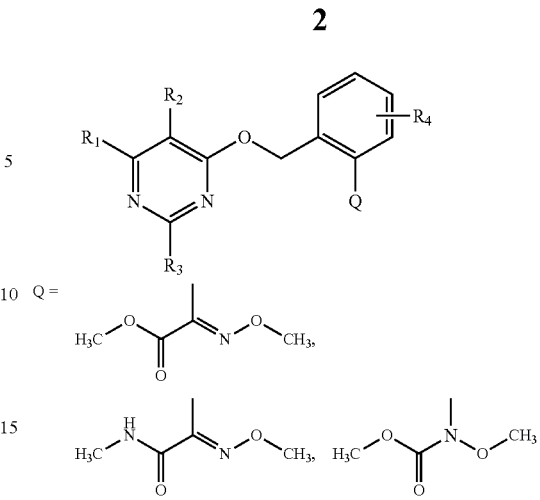

The compounds having the following general formula used as acaricides, fungicides were disclosed in WO2008145052A1 or CN101311170A by applicants of this invention:

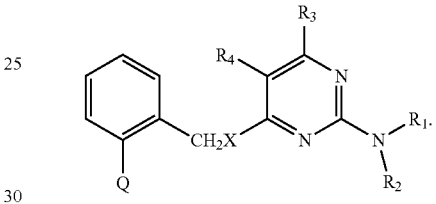

Although similar patents have existed already, the compounds with better insecticidal and acaricidal activities are still needed to be discovered and developed to control harmful insects and mites in agricultural, civil and zoic technical fields.

SUMMARY OF THE INVENTION

The object of the present invention is to provide a kind of E-type phenyl acrylic ester compounds containing substituted anilino pyrimidine group against harmful insects and mites at very low doses in agricultural, civil and zoic technical fields. Through detailed study, the compounds of the present invention showed not only good control against adults and nymphs of mites, but also excellent activity against eggs of mites.

Detailed descriptions of the invention are as follows:

The present invention provides a kind of E-type phenyl acrylic ester compounds containing substituted anilino pyrimidine group having general formula I:

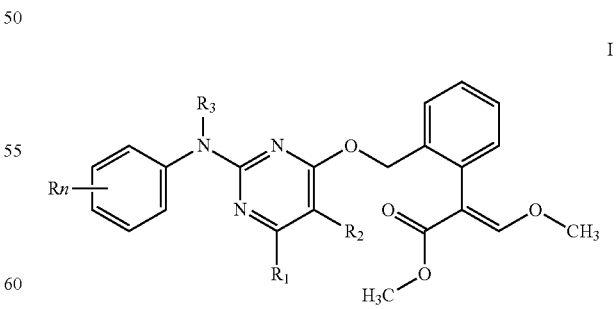

I

Wherein:
$R_1$ is selected from $C_1$-$C_3$haloalkyl;
$R_2$ is selected from H, halogen, CN, $NO_2$, $C_1$-$C_{12}$alkyl, $C_1$-$C_{12}$alkoxy, $C_1$-$C_{12}$haloalkoxy, $C_1$-$C_{12}$alkylthio or $C_1$-$C_{12}$alkylsulfonyl;

Or $R_1$, $R_2$ and pyrimidine ring compose a 5,6,7-trihydrocyclopentapyrimidine ring or 5,6,7,8-tetrahydrocyclohexapyrimidine ring;

$R_3$ is selected from H, CN, $C_1$-$C_{12}$alkyl, $C_1$-$C_{12}$haloalkyl, $C_3$-$C_6$cycloalkyl, $C_1$-$C_{12}$alkoxy, $C_1$-$C_{12}$haloalkoxy, $C_1$-$C_{12}$alkylthio, $C_1$-$C_{12}$alkylsulfonyl, $C_1$-$C_{12}$alkylcarbonyl, $C_1$-$C_{12}$alkoxyC_1$-$C_{12}$alkyl, $C_1$-$C_{12}$alkoxycarbonyl, $C_1$-$C_{12}$alkoxycarbonylC_1$-$C_{12}$ alkyl, or the following groups unsubstituted or substituted with 1-5 substitutents selected independently from halogen, $NO_2$, CN, $C_1$-$C_4$alkyl, $C_1$-$C_4$haloalkyl, $C_1$-$C_4$alkoxy, $C_1$-$C_4$haloalkoxy or $C_1$-$C_4$alkylthio: phenyl, benzyl, phenylcarbonyl, benzylcarbonyl, phenylsulfonyl or benzylsulfonyl;

R is selected from halogen, CN, $NO_2$, $C_1$-$C_4$alkyl or $C_1$-$C_3$haloalkyl, n=0-5;

Or their salts.

The preferred compounds of general formula I of this invention are:

$R_1$ is selected from $CCl_3$, $CF_2Cl$, $CFCl_2$, $CF_3$ or $CH_2CF_3$;

$R_2$ is selected from H, Cl or $CH_3$;

Or $R_1$, $R_2$ and pyrimidine ring compose a 5,6,7-trihydrocyclopentapyrimidine ring or 5,6,7,8-tetrahydrocyclohexapyrimidine ring;

$R_3$ is selected from H, $C_1$-$C_4$alkyl, $C_1$-$C_4$ alkylsulfonyl or $C_1$-$C_4$alkylcarbonyl;

When $R_2$ is H, Rn is selected from 2,3-difluoro, 2,4-difluoro, 2,4-dichloro, 2-fluoro-3-chloro, 2-chloro-3-fluoro, 2-fluoro-4-chloro, 2-chloro-4-fluoro, 2,3,4-trifluoro, 2,3,4-trichloro, 2,4-difluoro-3-methyl, 2,4-dichloro-3-methyl, 2-fluoro-3,4-dichloro or 2-chloro-3,4-difluoro;

When $R_2$ is selected from Cl or $CH_3$, Rn is selected from H, 2-chloro, 4-chloro, 2,3-difluoro, 2,4-difluoro, 2,3-dichloro, 2,4-dichloro, 2-fluoro-3-chloro, 2-chloro-3-fluoro, 2-fluoro-4-chloro, 2-chloro-4-fluoro, 2,3,4-trifluoro, 2,3,4-trichloro, 2,4-difluoro-3-methyl, 2,4-dichloro-3-methyl, 2-fluoro-3,4-dichloro or 2-chloro-3,4-difluoro;

When $R_1$, $R_2$ and pyrimidine ring compose a 5,6,7-trihydrocyclopentapyrimidine ring or 5,6,7,8-tetrahydrocyclohexapyrimidine ring, R is selected from halogen, CN, $NO_2$, $C_1$-$C_4$alkyl or $C_1$-$C_3$haloalkyl, n=0-4.

Or their hydrochloride, phosphate, acetate, benzene sulfonate or oxalate salts.

Furthermore, the preferred compounds of general formula I of this invention are:

$R_1$ is $CF_3$;

$R_2$ is selected from H, $C_1$ or $CH_3$;

Or $R_1$, $R_2$ and pyrimidine ring compose a 5,6,7-trihydrocyclopentapyrimidine ring or 5,6,7,8-tetrahydrocyclohexapyrimidine ring;

$R_3$ is H;

When $R_2$ is H, Rn is selected from 2,4-difluoro, 2,4-dichloro, 2-fluoro-4-chloro, 2-chloro-4-fluoro, 2,3,4-trifluoro, 2,3,4-trichloro or 2,4-dichloro-3-methyl;

When $R_2$ is selected from $C_1$ or $CH_3$, Rn is selected from H, 2-chloro, 4-chloro, 2,4-difluoro, 2,3-dichloro, 2,4-dichloro, 2-fluoro-4-chloro, 2-chloro-4-fluoro, 2,3,4-trifluoro, 2,3,4-trichloro or 2,4-dichloro-3-methyl;

When $R_1$, $R_2$ and pyrimidine ring compose a 5,6,7-trihydrocyclopentapyrimidine ring or 5,6,7,8-tetrahydrocyclohexapyrimidine ring, R is selected from chloro, bromo, fluoro, $C_1$-$C_4$alkyl or $C_1$-$C_3$haloalkyl, n=0-3;

Or their hydrochloride, phosphate, acetate, benzene sulfonate or oxalate salts.

It must be noted that, as used in this specification, the appended claims and the general formula I:

The "halogen" or "halo" is fluorine, chlorine, bromine or iodine.

The "alkyl" stands for straight or branched chain alkyl, such as methyl, ethyl, propyl, isopropyl or tert-butyl.

The "cycloalkyl" is substituted or unsubstituted cyclic alkyl, such as cyclopropyl, cyclopentyl or cyclohexyl. The substitute(s) is(are) methyl, halogen etc.

The "haloalkyl" stands for straight or branched chain alkyl, in which hydrogen atoms can be all or partly substituted with halogen, such as chloromethyl, dichloromethyl, trichloromethyl, fluoromethyl, difluoromethyl, trifluoromethyl etc.

The "alkoxy" refers to straight or branched chain alkyl, which is linked to the structure by oxygen atom.

The "haloalkoxy" refers to straight or branched chain alkoxy, in which hydrogen atoms may be all or partly substituted with halogen, such as chloromethoxy, dichloromethoxy, trichloromethoxy, fluoromethoxy, difluoromethoxy, trifluoromethoxy, chlorofluoromethoxy, trifluoroethoxy etc.

The alkylthio refers to straight or branched chain alkyl, which is linked to the structure by sulfur atom.

The present invention is also explained by the following compounds in Tables 1-3, but without being restricted thereby, the substitutes of phenyl ring Rn in formula I are denoted by $R_4$, $R_5$, $R_6$ and $R_7$.

TABLE 1

($R_1$ is $CF_3$)

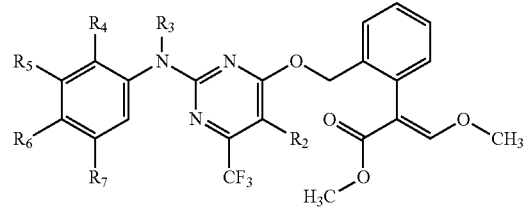

| Compd. NO. | $R_2$ | $R_3$ | $R_4$ | $R_5$ | $R_6$ | $R_7$ |
|---|---|---|---|---|---|---|
| 1 | H | H | H | H | CN | H |
| 2 | H | H | F | H | H | H |
| 3 | H | H | Br | H | H | H |
| 4 | H | H | CN | H | H | H |
| 5 | H | H | $NO_2$ | H | H | H |
| 6 | H | H | H | $CH_3$ | H | H |
| 7 | H | H | H | $CF_3$ | H | H |
| 8 | H | H | F | H | F | H |
| 9 | H | H | Cl | H | Cl | H |
| 10 | H | H | H | Cl | Cl | H |
| 11 | H | H | $NO_2$ | H | $NO_2$ | H |
| 12 | H | H | F | H | Cl | H |
| 13 | H | H | H | Cl | F | H |
| 14 | H | H | H | F | H | Cl |
| 15 | H | H | F | F | F | H |
| 16 | H | H | Cl | Cl | Cl | H |
| 17 | H | H | Cl | $CH_3$ | Cl | H |
| 18 | H | H | Cl | H | H | Cl |
| 19 | H | H | H | Cl | H | F |
| 20 | H | H | F | F | H | H |
| 21 | H | H | H | F | F | H |
| 22 | H | H | Br | Br | H | H |
| 23 | H | H | Br | H | Br | H |
| 24 | H | H | H | Br | Br | H |
| 25 | H | H | $CH_3$ | $CH_3$ | H | H |
| 26 | H | H | F | Cl | H | H |
| 27 | H | H | H | F | Cl | H |
| 28 | H | H | Cl | F | H | H |
| 29 | H | H | Cl | H | F | H |
| 30 | H | H | Cl | H | $CH_3$ | H |
| 31 | H | H | Cl | $CH_3$ | H | H |
| 32 | H | H | Br | Br | Br | H |
| 33 | H | $CH_3$ | F | H | H | H |
| 34 | H | $CH_3$ | Cl | H | H | H |

TABLE 1-continued ($R_1$ is $CF_3$)

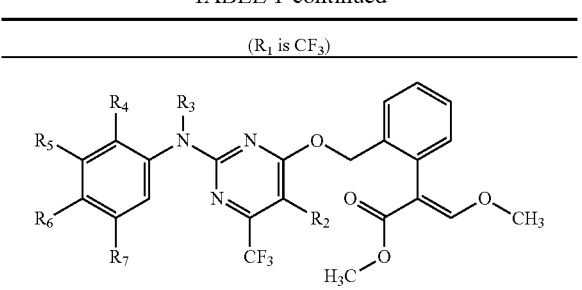

| Compd. NO. | $R_2$ | $R_3$ | $R_4$ | $R_5$ | $R_6$ | $R_7$ |
|---|---|---|---|---|---|---|
| 35 | H | $CH_3$ | F | F | H | H |
| 36 | H | $CH_3$ | Cl | Cl | H | H |
| 37 | H | $CH_3$ | F | H | F | H |
| 38 | H | $CH_3$ | Cl | H | Cl | H |
| 39 | H | $CH_3$ | F | H | Cl | H |
| 40 | H | $CH_3$ | Cl | H | F | H |
| 41 | H | $CH_3$ | F | F | F | H |
| 42 | H | $CH_3$ | Cl | Cl | Cl | H |
| 43 | H | $C_2H_5$ | F | H | H | H |
| 44 | H | $C_2H_5$ | Cl | H | H | H |
| 45 | H | $C_2H_5$ | F | F | H | H |
| 46 | H | $C_2H_5$ | Cl | Cl | H | H |
| 47 | H | $C_2H_5$ | F | H | F | H |
| 48 | H | $C_2H_5$ | Cl | H | Cl | H |
| 49 | H | $C_2H_5$ | F | H | Cl | H |
| 50 | H | $C_2H_5$ | Cl | H | F | H |
| 51 | H | $C_2H_5$ | F | F | F | H |
| 52 | H | $C_2H_5$ | Cl | Cl | Cl | H |
| 53 | H | $CH(CH_3)_2$ | F | H | H | H |
| 54 | H | $CH(CH_3)_2$ | Cl | H | H | H |
| 55 | H | $CH(CH_3)_2$ | F | F | H | H |
| 56 | H | $CH(CH_3)_2$ | Cl | Cl | H | H |
| 57 | H | $CH(CH_3)_2$ | F | H | F | H |
| 58 | H | $CH(CH_3)_2$ | Cl | H | Cl | H |
| 59 | H | $CH(CH_3)_2$ | F | H | Cl | H |
| 60 | H | $CH(CH_3)_2$ | Cl | H | F | H |
| 61 | H | $CH(CH_3)_2$ | F | F | F | H |
| 62 | H | $CH(CH_3)_2$ | Cl | Cl | Cl | H |
| 63 | H | $COCH_3$ | F | H | H | H |
| 64 | H | $COCH_3$ | Cl | H | Cl | H |
| 65 | H | $COCH_3$ | F | H | F | H |
| 66 | H | $COCH_3$ | F | F | F | H |
| 67 | H | $SO_2CH_3$ | F | H | H | H |
| 68 | H | $SO_2CH_3$ | Cl | H | Cl | H |
| 69 | H | $SO_2CH_3$ | F | H | F | H |
| 70 | H | $SO_2CH_3$ | F | F | F | H |
| 71 | Cl | H | F | H | H | H |
| 72 | Cl | H | Cl | H | Cl | H |
| 73 | Cl | H | F | H | F | H |
| 74 | Cl | H | F | F | F | H |
| 75 | Br | H | Cl | H | Cl | H |
| 76 | Br | H | F | H | F | H |
| 77 | Br | H | F | F | F | H |
| 78 | $CH_3$ | H | Cl | H | Cl | H |
| 79 | $CH_3$ | H | F | H | F | H |
| 80 | $CH_3$ | H | F | F | F | H |
| 81 | $CH_3$ | H | Cl | Cl | H | H |
| 82 | $CH_3$ | H | Cl | H | H | H |
| 83 | $CH_3$ | H | H | H | Cl | H |
| 84 | $CH_3$ | H | H | H | H | H |
| 85 | Cl | H | H | H | H | H |
| 86 | Cl | H | Cl | H | H | H |
| 87 | Cl | H | Cl | $CH_3$ | Cl | H |

TABLE 2

($R_1$, $R_2$ and pyrimidine ring compose a 5,6,7-trihydrocyclopentapyrimidine ring)

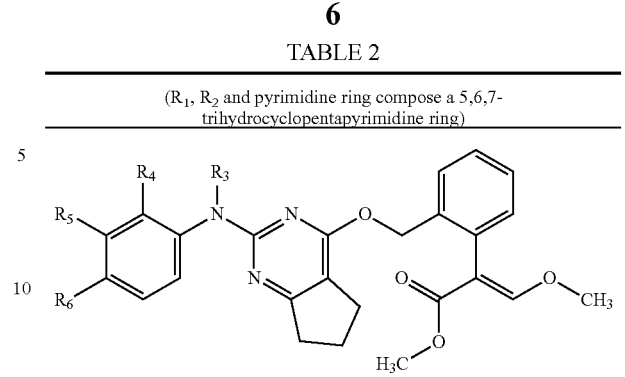

| Compd. NO. | $R_3$ | $R_4$ | $R_5$ | $R_6$ |
|---|---|---|---|---|
| 88 | H | H | H | H |
| 89 | H | H | H | CN |
| 90 | H | F | H | H |
| 91 | H | Cl | H | H |
| 92 | H | $CH_3$ | H | H |
| 93 | H | $OCH_3$ | H | H |
| 94 | H | H | $CH_3$ | H |
| 95 | H | H | $CF_3$ | H |
| 96 | H | F | H | F |
| 97 | H | Cl | H | Cl |
| 98 | H | H | Cl | Cl |
| 99 | H | $NO_2$ | H | $NO_2$ |
| 100 | H | F | H | Cl |
| 101 | H | H | Cl | F |
| 102 | H | $CH_3$ | Cl | H |
| 103 | H | F | F | F |
| 104 | H | Cl | Cl | Cl |
| 105 | H | Cl | $CH_3$ | Cl |
| 106 | H | F | F | H |
| 107 | H | H | F | F |
| 108 | H | Br | Br | H |
| 109 | H | Br | H | Br |
| 110 | H | H | Br | Br |
| 111 | H | $CH_3$ | $CH_3$ | H |
| 112 | H | F | Cl | H |
| 113 | H | H | F | Cl |
| 114 | H | Cl | F | H |
| 115 | H | Cl | H | F |
| 116 | H | Cl | H | $CH_3$ |
| 117 | H | Cl | $CH_3$ | H |
| 118 | H | Br | Br | Br |
| 119 | $CH_3$ | Cl | H | Cl |
| 120 | $CH_3$ | F | H | F |
| 121 | $CH_3$ | F | F | F |
| 122 | $CH_2C_2H_5$ | Cl | H | Cl |
| 123 | $CH(CH_3)_2$ | F | H | F |
| 124 | $CH(CH_3)_2$ | F | F | F |
| 125 | $COCH_3$ | Cl | H | Cl |
| 126 | $COCH_3$ | F | H | F |
| 127 | $COCH_3$ | F | F | F |
| 128 | H | Cl | Cl | H |

TABLE 3

($R_1$, $R_2$ and pyrimidine ring compose a 5,6,7,8-tetrahydrocyclohexapyrimidine ring)

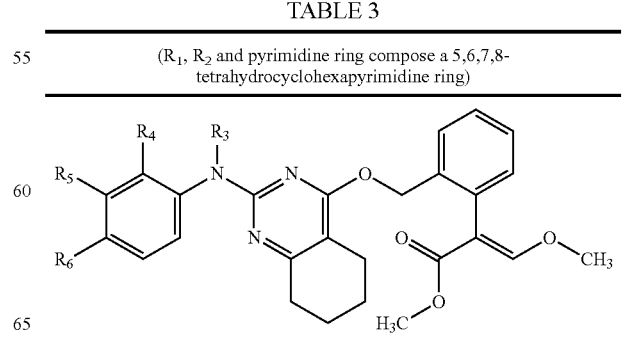

The substitutes of compounds 129-169 in table 3 are respectively the same as those of compounds 88-128 in table 2 in sequence.

The compounds represented by the general formula I of the present invention were prepared by the following method:

The compounds represented by the general formula I were prepared by reaction of pyrimidine compounds containing hydroxy group having general formula III with halomethylbenzene having general formula IV in the presence of base:

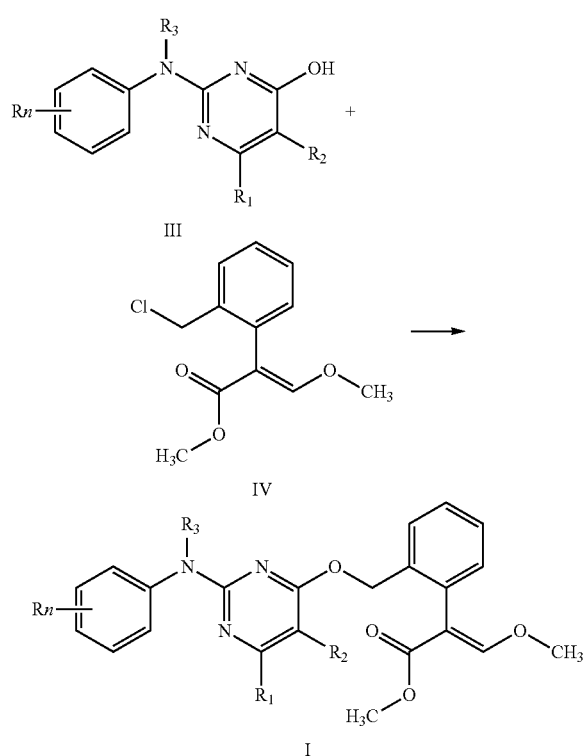

The halomethylbenzene IV can be prepared according to the known methods disclosed in U.S. Pat. No. 5,663,370, etc.

The reaction can be carried out in proper solvent, the proper solvent mentioned may be selected from tetrahydrofuran, acetonitrile, toluene, xylene, benzene, DMF, DMSO, acetone or butanone and so on.

The proper base mentioned above may be selected from potassium hydroxide, sodium hydroxide, sodium carbonate, potassium carbonate, sodium bicarbonate, triethylamine, pyridine, sodium methoxide, sodium ethoxide, sodium hydride, potassium tert-butoxide or sodium tert-butoxide and so on.

The proper temperature mentioned above is from room temperature to boiling point of solvent, normal temperature is from 20 to 100° C.

The reaction time is in the range of 30 minutes to 20 hours, generally being 1-10 hours.

The present invention also includes salts of compounds having general formula I, namely salts prepared by reaction of 2-amino of pyrimidine groups with corresponding acids, which can be obtained from the compounds of formula I reacting with corresponding acids according to the known methods. Salts of the compounds having general formula I can be inorganic salts such as hydrochlorides or phosphates and so on; or organic salts such as acetates, benzene sulfonates or oxalates and so on.

Intermediates of general formula III can be prepared by condensation reaction of intermediate of general formula II with β-ketoesters (such as ethyl 4,4,4-trifluoro-3-oxobutanoate etc.) according to the known methods, referring to GB1388402, U.S. Pat. No. 4,000,138, CH395385, etc.

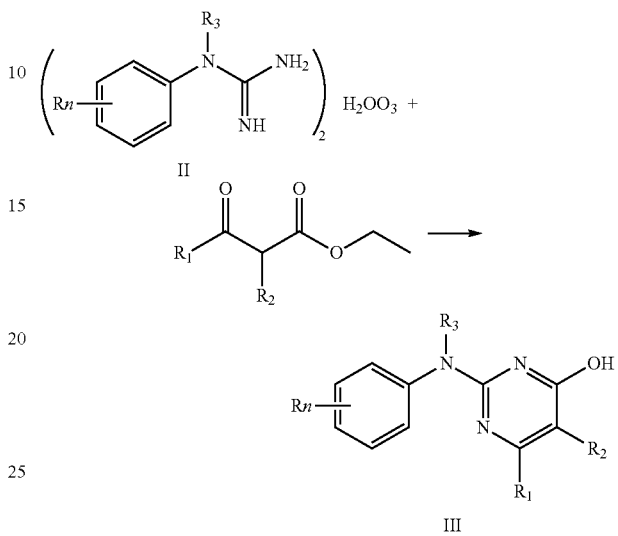

Intermediates of general formula II can be purchased or prepared according to the known methods, referring to EP310550, EP0655441, etc.

Some of intermediates III are listed in Table 4-Table 6:

TABLE 4

| NO. | $R_2$ | $R_3$ | $R_4$ | $R_5$ | $R_6$ | $R_7$ | m.p. (° C.) |
|---|---|---|---|---|---|---|---|
| III-1 | H | H | H | H | CN | H | 242-245 |
| III-2 | H | H | F | H | H | H | 232-234 |
| III-3 | H | H | Br | H | H | H | |
| III-4 | H | H | CN | H | H | H | |
| III-5 | H | H | $NO_2$ | H | H | H | |
| III-6 | H | H | H | $CH_3$ | H | H | 196-198 |
| III-7 | H | H | H | $CF_3$ | H | H | 180-182 |
| III-8 | H | H | F | H | F | H | 243-244 |
| III-9 | H | H | Cl | H | Cl | H | 253-254 |
| III-10 | H | H | H | Cl | Cl | H | 234-238 |
| III-11 | H | H | $NO_2$ | H | $NO_2$ | H | 254-256 |
| III-12 | H | H | F | H | Cl | H | 257-259 |
| III-13 | H | H | Cl | F | H | H | 195-196 |
| III-14 | H | H | H | F | H | Cl | |
| III-15 | H | H | F | F | F | H | 210-212 |
| III-16 | H | H | Cl | Cl | Cl | H | 278-279 |
| III-17 | H | H | Cl | $CH_3$ | Cl | H | 269-271 |
| III-18 | H | H | Cl | H | H | Cl | 196-197 |
| III-19 | H | H | H | Cl | H | F | |
| III-20 | H | $CH_3$ | F | H | F | H | |
| III-21 | H | $CH_3$ | Cl | H | Cl | H | |
| III-22 | H | $CH_3$ | F | H | Cl | H | |
| III-23 | H | $CH_3$ | F | F | F | H | |
| III-24 | H | $CH_3$ | Cl | Cl | Cl | H | |
| III-25 | H | $CH_3$ | Cl | $CH_3$ | Cl | H | |
| III-26 | H | $CH(CH_3)_2$ | F | H | F | H | |

TABLE 4-continued

Structure: R4, R3, R5, R6, R7 on phenyl ring, N(R3)—pyrimidine with OH, R2, CF3 substituents

| NO. | R$_2$ | R$_3$ | R$_4$ | R$_5$ | R$_6$ | R$_7$ | m.p. (° C.) |
|---|---|---|---|---|---|---|---|
| III-27 | H | CH(CH$_3$)$_2$ | Cl | H | Cl | H | |
| III-28 | H | CH(CH$_3$)$_2$ | F | H | Cl | H | |
| III-29 | H | CH(CH$_3$)$_2$ | F | F | F | H | |
| III-30 | H | CH(CH$_3$)$_2$ | Cl | Cl | Cl | H | |
| III-31 | H | CH(CH$_3$)$_2$ | Cl | CH$_3$ | Cl | H | |
| III-32 | CH$_3$ | H | Cl | H | Cl | H | decompose at 267° C. |
| III-33 | CH$_3$ | H | F | H | F | H | 205-207 |
| III-34 | CH$_3$ | H | F | F | F | H | 190-192 |
| III-35 | CH$_3$ | H | Cl | Cl | H | H | >280 |
| III-36 | CH$_3$ | H | Cl | H | H | H | decompose at 240° C. |
| III-37 | CH$_3$ | H | H | H | Cl | H | 210-212 |
| III-38 | CH$_3$ | H | H | H | H | H | 152-155 |
| III-39 | Cl | H | H | H | H | H | |
| III-40 | Cl | H | Cl | Cl | H | H | |
| III-41 | Cl | H | Cl | H | Cl | H | |
| III-42 | Cl | H | F | H | F | H | |
| III-43 | Cl | H | F | F | F | H | |

$^1$H-NMR spectrum ($^1$HNMR, 300 MHz, internal standard: TMS, solvent DMSO, δ(ppm)) of some intermediates in Table 4 are as follows:
Intermediate III-32: 2.00 (d, 3H), 7.35 (m, 1H), 7.55 (d, 1H), 8.25 (m, 1H), 8.80 (s, 1H).
Intermediate III-33: 2.00 (d, 3H), 7.00 (m, 1H), 7.18 (m, 1H), 8.20 (m, 1H), 8.72 (s, 1H).
Intermediate III-34: 2.01 (t, 3H), 7.18 (m, 1H), 7.95 (d, 1H), 8.91 (s, 1H).
Intermediate III-35: 2.01 (d, 3H), 7.29 (m, 2H), 8.24 (m, 1H), 8.90 (s, 1H).
Intermediate III-36: 2.00 (d, 3H), 7.06 (t, 1H), 7.28 (t, 1H), 7.41 (d, 1H), 8.34 (d, 1H).
Intermediate III-37: 2.01 (d, 3H), 7.29 (m, 2H), 7.63 (d, 2H), 9.07 (s, 1H).
Intermediate III-38: 2.00 (d, 3H), 7.03 (t, 1H), 7.29 (t, 2H), 7.60 (d, 2H), 8.96 (s, 1H).

TABLE 5

Structure: phenyl with R4, R3, R5, R6 substituents linked via N to pyrimidine fused cyclopentane with OH

| NO. | R$_3$ | R$_4$ | R$_5$ | R$_6$ | m.p. (° C.) |
|---|---|---|---|---|---|
| III-44 | H | H | H | H | 234-236 |
| III-45 | H | F | H | H | |
| III-46 | H | Cl | H | H | |
| III-47 | H | F | H | F | 217-218 |
| III-48 | H | Cl | H | Cl | decompose at 270° C. |
| III-49 | H | F | H | Cl | |
| III-50 | H | Cl | H | F | |
| III-51 | H | F | F | F | decompose at 238° C. |
| III-52 | H | Cl | Cl | Cl | |
| III-53 | H | Cl | CH$_3$ | Cl | decompose at 245° C. |
| III-54 | H | Cl | Cl | H | decompose at 270° C. |

$^1$H-NMR spectrum ($^1$HNMR, 300 MHz, internal standard: TMS, solvent DMSO, δ(ppm)) of some intermediates in Table 5 are as follows:
Intermediate III-51: 1.95 (m, 2H), 2.56 (t, 2H), 2.65 (t, 2H), 7.19 (m, 1H), 7.94 (s, 1H).
Intermediate III-53: 2.08 (m, 2H), 2.60 (s, 3H), 2.71 (t, 2H), 2.83 (t, 2H), 7.32 (d, 1H), 7.63 (s, 1H), 7.80 (s, 1H).

TABLE 6

Structure: phenyl with R4, R3, R5, R6 substituents linked via N to pyrimidine fused cyclohexane with OH

| NO. | R$_3$ | R$_4$ | R$_5$ | R$_6$ | m.p. (° C.) |
|---|---|---|---|---|---|
| III-55 | H | H | H | H | 264-265 |
| III-56 | H | F | H | H | |
| III-57 | H | Cl | H | H | |
| III-58 | H | F | H | F | 242-244 |
| III-59 | H | Cl | H | Cl | 226-228 |
| III-60 | H | F | H | Cl | |
| III-61 | H | Cl | H | F | |
| III-62 | H | F | F | F | 276-278 |
| III-63 | H | Cl | Cl | Cl | |
| III-64 | H | Cl | CH$_3$ | Cl | decompose at 280° C. |
| III-65 | H | Cl | Cl | H | >280 |

$^1$H-NMR spectrum ($^1$HNMR, 300 MHz, internal standard: TMS, solvent DMSO, δ(ppm)) of some intermediates in Table 6 are as follows:
Intermediate III-55: 1.69 (m, 4H), 2.28 (t, 2H), 2.47 (m, 2H), 6.94 (t, 1H), 7.24 (t, 2H), 7.59 (d, 2H), 8.40 (s, 1H), 10.45 (s, 1H).
Intermediate III-58: 1.69 (m, 4H), 2.27 (t, 2H), 2.50 (t, 2H), 6.92 (t, 1H), 7.09 (t, 1H), 8.39 (m, 1H).
Intermediate III-62: 1.67 (m, 4H), 2.26 (t, 2H), 2.41 (t, 2H), 7.16 (m, 2H), 8.05 (d, 1H).
Intermediate III-64: 1.69 (m, 4H), 2.27 (t, 2H), 2.44 (d, 5H), 7.29 (d, 1H), 8.30 (d, 1H).
Intermediate III-65: 1.69 (m, 4H), 2.27 (t, 2H), 2.43 (t, 2H), 7.21 (m, 1H), 8.41 (d, 1H).

The compounds of general formula I showed high insecticidal activity to adults, nymphs and eggs of harmful insects and mites in agricultural, civil and zoic technical fields.

A further object of the present invention relates to the use of the compounds having general formula I to control insects and harmful mites in agriculture and other fields. In particular, the compounds having general formula I are active against important species of tetranychidae (Tetranychus urticae, Tetranychus cinnabarinus, Panonychus ulmi, Panonychus citri, etc.), eriophyidae, tarsonemidae, etc.

Meanwhile, the compounds having general formula I have a low toxicity to many useful insects and mites, mammals, fish and birds, furthermore, the compounds have no phytotoxicity.

Thanks to their positive characteristics, the compounds mentioned above can be advantageously used in protecting crops of farming and gardening, domestic and breeding animals, as well as environments frequented by human beings, from harmful mites and insects.

In order to obtain the desired effect, the dosage of compound to be applied can vary with various factors, for example, the used compound, the protected crop, the type of harmful organism, the degree of infestation, the climatic conditions, the application method and the adopted formulation.

Doses of compound in the range of 10 g to 5 kg per hectare generally can provide a sufficient control to the harmful mites and insects.

Another object of the present invention also relates to a method for controlling insects and/or phytopathogenic fungi in crops of farming and gardening and/or on domestic and breeding animals and/or environments frequented by human beings, by the application of the compounds having general formula I. In particular, the dosage of compounds to be applied varies from 10 g to 5 kg per hectare.

A further object of the present invention relates to insecticidal and/or acaricidal compositions containing one or more compounds having general formula I as active ingredient and acceptable carrier in agriculture, the weight percentage of the active ingredient in the composition is 0.5-90%.

Therefore another object of the present invention also relates to the use of the compositions mentioned above to control insects and harmful mites in agriculture and other fields.

For practical application in agriculture, it is usually beneficial to use compositions containing one or more compounds having general formula I.

Compositions can be used in the form of dry powders, wettable powders, emulsifiable concentrates, microemulsions, pastes, granulates, solutions, suspensions, etc. The selection of the type of compositions depends on the specific application.

The compositions are prepared in the known way, for example by diluting or dissolving the active substance with a solvent medium and/or a solid diluent, optionally in the presence of surface-active agents.

Solid diluents, or carriers which can be used are, for example: silica, kaolin, bentonite, talc, diatomite, dolomite, calcium carbonate, magnesia, chalk, clays, synthetic silicates, attapulgite, sepiolite.

Liquid diluents which can be used are, for example, besides water, aromatic organic solvents (xylols or mixtures of alkylbenzols, chlorobenzene, etc.), paraffins (petroleum fractions), alcohols (methanol, propanol, butanol, octanol, glycerin, etc.), esters (ethyl acetate, isobutyl acetate, etc.), ketones (cyclohexanone, acetone, acetophenone, isophorone, ethylamylketone, etc.), amides (N,N-dimethylformamide, N-methylpyrrolidone, etc.).

Surface-active agents which can be used are salts of sodium, calcium, triethylamine or triethanolamine of alkylsulfonates, alkylarylsulfonates, polyethoxylated alkylphenols, polyethoxylated esters of sorbitol, ligninsulfonates, etc.

The compositions can also contain special additives for particular purposes, for example adhesion agents such as Arabic gum, polyvinyl alcohol, polyvinyl-pyrrolidone, etc.

The concentration of active ingredient in the above compositions can vary within a wide range depending on the active compound, the applications for which they are destined, the environmental conditions and the type of adopted formulation. In general the concentration of active ingredient ranges from 1% to 90%, preferably from 5% to 50%.

If required, other active ingredients being compatible with the compounds having general formula I can be added to the compositions, such as, other acaricides/insecticides, fungicides, plant growth regulators, antibiotics, herbicides, fertilizers.

The preparation methods of several common formulations examples in the present invention are as follows:

The preparation of suspension concentrate: the common active component in formula is 5%-35%. With water as the medium, the compound in the invention, dispersing agent, suspending agent and antifreeze are added to sanding machine for grinding to make suspension concentrate.

The preparation of wettable powder: according to formulation requirements, the compound in the invention, surfactants and solid diluents are mixed well, after smashing through ultrafine pulverizer, which is the wettable powder products (for example, 10%-60%). For the preparation of the spraying wettable powder, the compounds of this invention can be formed the mixture with solid powder, such as clay, inorganic silicates, carbonates, as well as wetting agents, adhesives and/or dispersant agent.

The preparation of water dispersible granules: the compound in the invention and powdered solid diluents, wetting agents and adhesives are mixed to smash, kneading together with water, added to the granulation machine with 10 to 100 mesh for granulation, then by drying and sieving (at the scope screen). Also, the compound, in the invention dispersants, disintegrants, wetting agents and solid diluent are added to sanding machine, grinding in water to produce suspension and then spray-drying granulation, usually the content of the prepared granular products is 20%-30%.

DETAILED DESCRIPTION OF THE INVENTION

The following examples are illustrative of the present invention, but without being restricted thereby.

PREPARATION EXAMPLES

Example 1

The Preparation of Compound 9

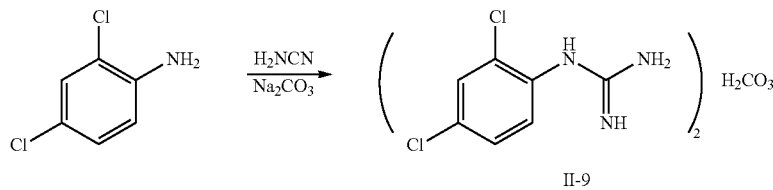

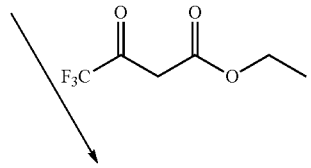

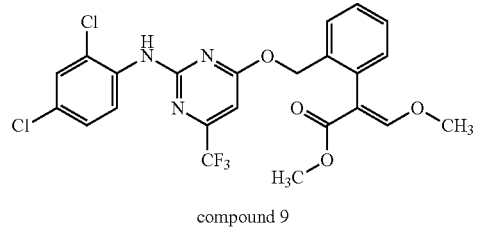 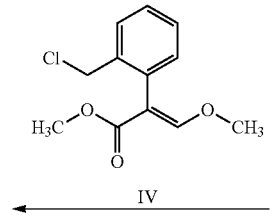 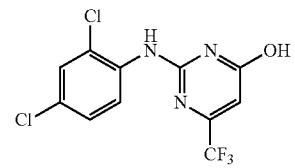

compound 9     IV     III-9

1) The Preparation of 1-(2,4-dichlorophenyl)guanidine II-9

2 g of concentrated hydrochloric acid was added dropwise to a reaction flask with 3.28 g of 2,4-dichloroaniline, the pH was kept between 2-3, 2.02 g of 50% aqueous cyanamide was added after the temperature was raised to 85° C. and all of the solid was dissolved. The reaction mixture was stirred at 85° C. for 5 hours with the increase of pH (about 7), and then was cooled to 60° C. 10.6 g of 10% aqueous sodium carbonate was added dropwise, after completion of addition, the reaction mixture was stirred for another 10 minutes and cooled, the solid was filtered, washed with water and dried to give 3.95 g of milky white solid.

2) The Preparation of Intermediate III-9

2.35 g of 1-(2,4-dichlorophenyl)guanidine II-9 and 30 ml of toluene were added to a 100 ml reaction flask with water segregator, the reaction mixture was heated to 100° C. or so. 2.02 g of ethyl trifluoroacetoacetate was added dropwise after all solid was dissolved and no more gas was released. After completion of addition, the reaction mixture was heated to reflux until no more water drop from condensation pipe, and then continued refluxing for another 30 minutes and then cooled, the precipitate was filtered and washed with a little toluene to give 2.96 g of white cottony solid, m.p. 253-254° C.

3) The Preparation of Compound 9

0.65 g of intermediate 111-9 was dissolved in 15 ml of DMF, 0.55 g of potassium carbonate was added, after the reaction mixture was stirred for half an hour at room temperature, 0.44 g of intermediate IV (prepared according to U.S. Pat. No. 5,663,370) was added, the reaction mixture was heated to 80° C. for 8 hours. After the reaction was over by Thin-Layer Chromatography monitoring, the reaction mixture was poured into 30 ml of saturated brine and extracted with ethyl acetate, the extract was dried over anhydrous magnesium sulfate and concentrated under reduced pressure. The crude product was purified through silica column (ethyl acetate/petroleum ether (boiling point range 60-90° C.)=1/10, as an eluent) to give light yellow solid, 10 ml of petroleum ether was added to the solid, and then the solid was filtered to obtain 0.71 g of milky white solid (compound 9), m.p. 120-121° C.

$^1$H-NMR spectrum (300 MHz, internal standard: TMS, solvent CDCl$_3$) δ (ppm): 3.68 (s, 3H), 3.79 (s, 3H), 5.34 (s, 2H), 6.56 (s, 1H), 7.20 (m, 1H), 7.25 (m, 1H), 7.36 (m, 2H), 7.41 (m, 1H), 7.50 (m, 1H), 7.57 (s, 1H), 7.60 (s, 1H), 8.40 (d, 1H).

Example 2

The Preparation of Compound 88

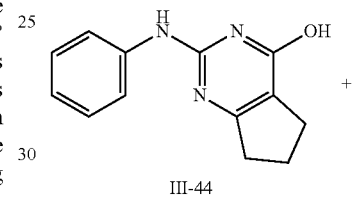

III-44

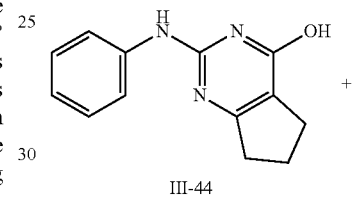

IV

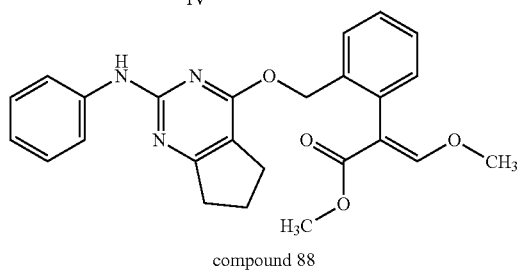

compound 88

0.48 g of intermediate 111-44 (prepared according to Example 1) was dissolved in 10 ml of DMF, 0.55 g of potassium carbonate was added, after the reaction mixture was stirred for half an hour at room temperature, 0.44 g of intermediate IV was added, the reaction mixture was heated to 80° C. for 8 hours. After the reaction was over by Thin-Layer Chromatography monitoring, the reaction mixture was poured into 30 ml of saturated brine and extracted with ethyl acetate, the extract was dried over anhydrous magnesium sulfate and concentrated under reduced pressure. The crude product was purified through silica column (ethyl acetate/petroleum ether (boiling point range 60-90° C.)=1/10, as an eluent) to give light yellow solid, 10 ml of petroleum ether was added to the solid, and then the solid was filtered to obtain 0.50 g of milky white solid (compound 88), m.p. 161-163° C.

$^1$H-NMR spectrum (300 MHz, internal standard: TMS, solvent CDCl$_3$) δ (ppm): 2.07 (m, 2H), 2.77 (t, 2H), 2.85 (t, 2H), 3.68 (s, 3H), 3.75 (s, 3H), 5.35 (s, 2H), 6.98 (m, 1H), 7.19 (m, 1H), 7.34 (m, 4H), 7.55 (m, 1H), 7.57 (s, 1H), 7.63 (m, 2H).

Other compounds of general formula I of the present invention were prepared according the above examples.

Physical properties and $^1$HNMR spectrum ($^1$HNMR, 300 MHz, internal standard: TMS, solvent CDCl$_3$) of some compounds having the general formula I of this invention are as follows:

Compound 1: m.p. 151-154° C. δ (ppm): 3.77 (s, 3H), 3.84 (s, 3H), 5.30 (s, 2H), 6.60 (s, 1H), 7.20 (m, 1H), 7.34 (m, 2H), 7.46 (m, 1H), 7.58 (m, 2H), 7.64 (s, 1H), 7.82 (m, 2H), 7.92 (m, 1H).

Compound 2: m.p. 89-91° C. δ (ppm): 3.69 (s, 3H), 3.78 (s, 3H), 5.35 (s, 2H), 6.53 (s, 1H), 7.00 (m, 1H), 7.18 (m, 4H), 7.35 (m, 2H), 7.49 (m, 2H), 7.57 (s, 1H).

Compound 6: m.p. 98-100° C. δ (ppm): 2.34 (s, 1H), 3.69 (s, 3H), 3.76 (s, 3H), 5.32 (s, 2H), 6.46 (s, 1H), 6.88 (m, 1H), 7.22 (m, 2H), 7.36 (m, 4H), 7.49 (m, 2H), 7.57 (s, 1H).

Compound 7: m.p. 108-110° C. δ (ppm): 3.73 (s, 3H), 3.80 (s, 3H), 5.30 (s, 2H), 6.53 (s, 1H), 7.20 (m, 1H), 7.34 (m, 3H), 7.42 (m, 2H), 7.60 (s, 1H), 7.81 (d, 2H), 8.06 (s, 1H).

Compound 8: m.p. 105-107° C. δ (ppm): 3.70 (s, 3H), 3.80 (s, 3H), 5.31 (s, 2H), 6.54 (s, 1H), 6.90 (m, 2H), 7.20 (m, 1H), 7.28 (m, 1H), 7.36 (m, 2H), 7.48 (m, 1H), 7.59 (s, 1H), 8.28 (m, 1H).

Compound 10: m.p. 188-190° C. δ (ppm): 3.74 (s, 3H), 3.81 (s, 3H), 5.30 (s, 2H), 6.52 (s, 1H), 7.20 (m, 1H), 7.33 (m, 3H), 7.48 (m, 2H), 7.61 (m, 2H), 7.90 (m, 1H).

Compound 11: m.p. 165-168° C. δ (ppm): 3.67 (s, 3H), 3.83 (s, 3H), 5.42 (s, 2H), 6.77 (s, 1H), 7.20 (m, 1H), 7.38 (m, 2H), 7.51 (m, 1H), 7.61 (s, 1H), 8.48 (m, 1H), 9.20 (m, 2H), 10.85 (s, 1H).

Compound 12: m.p. 118-120° C. δ (ppm): 3.70 (s, 3H), 3.80 (s, 3H), 5.33 (s, 2H), 6.56 (s, 1H), 7.12 (m, 1H), 7.15 (m, 1H), 7.20 (m, 1H), 7.37 (m, 3H), 7.50 (m, 1H), 7.59 (s, 1H), 8.37 (m, 1H).

Compound 13: m.p. 135-137° C. δ (ppm): 3.73 (s, 3H), 3.82 (s, 3H), 5.28 (s, 2H), 6.51 (s, 1H), 7.09 (m, 1H), 7.20 (m, 1H), 7.34 (m, 2H), 7.47 (m, 2H), 7.61 (s, 1H), 7.82 (m, 1H).

Compound 15: m.p. 129-130° C. δ (ppm): 3.71 (s, 3H), 3.80 (s, 3H), 5.31 (s, 2H), 6.57 (s, 1H), 6.98 (m, 1H), 7.20 (m, 1H), 7.30 (m, 1H), 7.36 (m, 2H), 7.48 (m, 1H), 7.59 (s, 1H), 8.06 (s, 1H).

Compound 16: δ (ppm): 3.69 (s, 3H), 3.80 (s, 3H), 5.34 (s, 2H), 6.59 (s, 1H), 7.21 (m, 1H), 7.38 (m, 3H), 7.50 (m, 1H), 7.59 (s, 1H), 7.68 (m, 1H), 8.40 (d, 1H).

Compound 17: m.p. 115-117° C. δ (ppm): 2.52 (s, 3H), 3.68 (s, 3H), 3.78 (s, 3H), 5.34 (s, 2H), 6.55 (s, 1H), 7.19 (m, 1H), 7.29 (d, 1H), 7.37 (m, 2H), 7.49 (m, 2H), 7.57 (s, 1H), 7.74 (s, 1H), 8.24 (d, 1H).

Compound 18: m.p. 115-117° C. δ (ppm): 3.67 (s, 3H), 3.79 (s, 3H), 5.37 (s, 2H), 6.57 (s, 1H), 6.99 (m, 1H), 7.19 (m, 1H), 7.37 (m, 3H), 7.52 (m, 1H), 7.58 (s, 1H), 7.63 (m, 1H), 8.65 (d, 1H).

Compound 78: 熔点 160-162° C. δ (ppm): 2.19 (d, 3H), 3.69 (s, 3H), 3.80 (s, 3H), 5.34 (s, 2H), 7.23 (m, 2H), 7.38 (m, 3H), 7.50 (m, 2H), 7.58 (s, 1H), 8.49 (d, 1H).

Compound 79: m.p. 129-131° C. δ (ppm): 2.19 (d, 3H), 3.68 (s, 3H), 3.80 (s, 3H), 5.32 (s, 2H), 6.89 (m, 1H), 7.13 (m, 1H), 7.20 (m, 1H), 7.37 (m, 2H), 7.51 (m, 1H), 7.60 (s, 1H), 8.19 (m, 1H).

Compound 80: m.p. 156-158° C. δ (ppm): 2.20 (d, 3H), 3.71 (s, 3H), 3.82 (s, 3H), 5.32 (s, 2H), 6.97 (m, 1H), 7.15 (m, 1H), 7.21 (m, 1H), 7.37 (m, 2H), 7.51 (m, 1H), 7.60 (s, 1H), 8.19 (m, 1H).

Compound 81: m.p. 160-162° C. δ (ppm): 2.19 (d, 3H), 3.68 (s, 3H), 3.80 (s, 3H), 5.35 (s, 2H), 7.14 (m, 1H), 7.22 (m, 2H), 7.38 (m, 2H), 7.54 (m, 1H), 7.58 (s, 1H), 7.63 (s, 1H), 8.50 (d, 1H).

Compound 82: m.p. 142-144° C. δ (ppm): 2.18 (d, 3H), 3.68 (s, 3H), 3.77 (s, 3H), 5.36 (s, 2H), 6.97 (m, 1H), 7.21 (m, 1H), 7.29 (m, 1H), 7.38 (m, 3H), 7.54 (m, 2H), 7.58 (s, 1H), 8.52 (d, 1H).

Compound 83: m.p. 167-170° C. δ (ppm): 2.19 (d, 3H), 3.72 (s, 3H), 3.81 (s, 3H), 5.26 (s, 2H), 7.21 (m, 1H), 7.34 (m, 4H), 7.49 (m, 1H), 7.58 (m, 1H), 7.61 (s, 2H).

Compound 84: m.p. 150-152° C. δ (ppm): 2.18 (d, 3H), 3.70 (s, 3H), 3.78 (s, 3H), 5.27 (s, 2H), 7.03 (m, 1H), 7.20 (m, 1H), 7.36 (m, 4H), 7.52 (m, 2H), 7.59 (s, 1H), 7.63 (s, 1H), 7.65 (s, 1H).

Compound 85: m.p. 141-143° C. δ (ppm): 3.70 (s, 3H), 3.79 (s, 3H), 5.38 (s, 2H), 7.07 (t, 1H), 7.20 (m, 1H), 7.35 (m, 3H), 7.44 (s, 1H), 7.54 (m, 1H), 7.63 (m, 3H).

Compound 96: m.p. 106-108° C. δ (ppm): 2.08 (m, 2H), 2.77 (t, 2H), 2.85 (t, 2H), 3.69 (s, 3H), 3.77 (s, 3H), 5.32 (s, 2H), 6.84 (m, 2H), 7.04 (m, 1H), 7.19 (m, 1H), 7.34 (m, 2H), 7.51 (m, 1H), 7.58 (s, 1H), 8.35 (m, 1H).

Compound 97: m.p. 150-151° C. δ (ppm): 2.05 (m, 2H), 2.78 (t, 2H), 2.87 (t, 2H), 3.68 (s, 3H), 3.77 (s, 3H), 5.34 (s, 2H), 7.20 (m, 2H), 7.35 (m, 3H), 7.40 (s, 1H), 7.52 (m, 1H), 7.57 (s, 1H), 8.44 (d, 1H).

Compound 103: m.p. 118-120° C. δ (ppm): 2.09 (m, 2H), 2.78 (t, 2H), 2.85 (t, 2H), 3.69 (s, 3H), 3.78 (s, 3H), 5.31 (s, 2H), 6.92 (m, 1H), 7.18 (s, 1H), 7.20 (m, 1H), 7.34 (m, 2H), 7.51 (m, 1H), 7.58 (s, 1H), 8.09 (m, 1H).

Compound 105: m.p. 150-151° C. δ (ppm): 2.09 (m, 2H), 2.49 (s, 3H), 2.78 (t, 2H), 2.87 (t, 2H), 3.68 (s, 3H), 3.77 (s, 3H), 5.34 (s, 2H), 7.24 (m, 2H), 7.35 (m, 2H), 7.53 (m, 2H), 7.57 (s, 1H), 8.32 (d, 1H).

Compound 128: m.p. 132-134° C. δ (ppm): 2.08 (m, 2H), 2.78 (t, 2H), 2.88 (t, 2H), 3.66 (s, 3H), 3.77 (s, 3H), 5.35 (s, 2H), 7.07 (m, 1H), 7.18 (m, 2H), 7.36 (m, 2H), 7.54 (m, 2H), 7.57 (s, 1H), 8.49 (d, 1H).

Compound 129: m.p. 136-138° C. δ (ppm): 1.81 (m, 4H), 2.55 (t, 2H), 2.70 (t, 2H), 3.71 (s, 3H), 3.78 (s, 3H), 5.37 (s, 2H), 6.98 (m, 1H), 7.22 (m, 1H), 7.38 (m, 4H), 7.58 (m, 1H), 7.61 (s, 1H), 7.66 (m, 2H).

Compound 137: m.p. 118-120° C. δ (ppm): 1.80 (m, 4H), 2.52 (t, 2H), 2.68 (t, 2H), 3.69 (s, 3H), 3.78 (s, 3H), 5.29 (s, 2H), 6.86 (m, 3H), 7.19 (m, 1H), 7.37 (m, 2H), 7.54 (m, 1H), 7.58 (s, 1H), 8.38 (m, 1H).

Compound 138: m.p. 170-171° C. δ (ppm): 1.80 (m, 4H), 2.52 (t, 2H), 2.69 (t, 2H), 3.68 (s, 3H), 3.78 (s, 3H), 5.30 (s, 2H), 7.19 (m, 2H), 7.28 (s, 1H), 7.35 (m, 3H), 7.54 (m, 1H), 7.58 (s, 1H), 8.48 (d, 1H).

Compound 144: m.p. 142-144° C. δ (ppm): 1.80 (m, 4H), 2.52 (t, 2H), 2.68 (t, 2H), 3.70 (s, 3H), 3.79 (s, 3H), 5.28 (s, 2H), 6.91 (m, 2H), 7.19 (m, 1H), 7.35 (m, 2H), 7.53 (m, 1H), 7.59 (s, 1H), 8.16 (m, 1H).

Compound 146: m.p. 170-172° C. δ (ppm): 1.80 (m, 4H), 2.49 (s, 3H), 2.52 (t, 2H), 2.69 (t, 2H), 3.69 (s, 3H), 3.78 (s, 3H), 5.30 (s, 2H), 7.20 (m, 2H), 7.35 (m, 3H), 7.54 (m, 1H), 7.58 (s, 1H), 8.16 (m, 1H).

Compound 169: m.p. 150-152° C. δ (ppm): 1.80 (m, 4H), 2.53 (t, 2H), 2.70 (t, 2H), 3.68 (s, 3H), 3.78 (s, 3H), 5.32 (s, 2H), 7.06 (m, 1H), 7.18 (m, 2H), 7.36 (m, 2H), 7.46 (s, 1H), 7.56 (m, 1H), 7.58 (s, 1H).

FORMULATION EXAMPLES

Base On 100% Active Ingredient (Weight/Weight %)

Example 3

15% Compound 9 Suspension Concentrate

| | |
|---|---|
| Compound 15 | 15% |
| Glycol | 4% |
| Nonylphenols polyethylene glycol ether | 3% |
| Lignin sulfonate | 4% |
| Carboxymethyl cellulose | 1% |
| 75% of silicone oil water emulsion | 0.8% |
| Water | Make up to 100% |

Fully mixing the compound 9 and other components, suspension concentrate can be obtained, and then any required concentration dilution can be obtained by diluting the above obtained concentrated suspension with water.

Example 4

30% Compound 9 Wettable Powders

| | |
|---|---|
| Compound 9 | 30% |
| Sodium dodecyl sulfate | 2% |
| Lignin sulfonate | 3% |
| Naphthalene sulfonic acid formaldehyde condensate | 5% |
| Precipitated calcium carbonate | Make up to 100% |

Compound 9 and other components are fully mixed, after smashing through ultrafine pulverizer, 30% compound 9 wettable powders products were obtained.

Example 5

60% Compound 88 Water Dispersible Granules

| | |
|---|---|
| Compound 88 | 60% |
| Naphthalene sulfonate formaldehyde condensate | 12% |
| Sodium-N-methyl-N-oleyl taurate | 8% |
| Polyvinylpyrrolidone | 2% |
| Carboxymethyl cellulose | 2% |
| Kaolin | Make up to 100% |

To mix compound 88 and other components, after smashing, kneading together with water, added to the granulation 10-100 mesh machine for granulation, then by drying and sieving (at the scope screen), that is, 60% water dispersible granules.

BIOLOGICAL TESTING

Example 6

Determination of Acaricidal Activity in Greenhouse

The activity determinations of compounds of the present invention against adults, nymphs and eggs of *Tetranychus cinnabarinus* were carried out in greenhouse by the following procedures:

The activity determination against adults in greenhouse: the compounds were weighed and dissolved in acetone to obtain mother liquid, and then the mother liquid was diluted to required concentration with placed running water containing 0.1% of Tween 80. Broadbean shoots with two true leaves were used to inoculate adults of *Tetranychus cinnabarinus* which were counted, spraying treatment was performed by portable sprayer (DeVilbiss Atomizer M163), 3 replicates were set for each treatment. After treatment the broadbean shoots were maintained in standard observation room. Scores were conducted and mortalities were calculated after 72 hrs.

The activity determination against nymphs in greenhouse: broadbean shoots with two true leaves in pot were taken, ten healthy female adults of *Tetranychus cinnabarinus* were inoculated to the leaves, the adults were removed after 24 hrs and the eggs were cultivated into nymphs after 7-10 days. The nymphs were counted and then sprayed. 3 replicates were set for each treatment. And then were maintained in standard observation room. Scores were conducted and mortalities were calculated after 72 hrs.

The activity determination against eggs in greenhouse: Broadbean shoots in pot with one true leaf retained were taken, ten healthy female adults of *Tetranychus cinnabarinus* were inoculated to the leaves, the adults were removed after 24 hrs and the eggs were counted and then sprayed. The treatment of test compounds and spaying method were the same as that of the activity determination in greenhouse against adults. Once eggs of blank control were all hatched after 5 days, unhatched eggs in each treatment were investigated and the hatching inhibition rate were calculated.

Parts of the test results are as follows:

At the dose of 100 mg/L, compounds 2, 6, 8, 9, 12, 13, 15, 16, 17, 18, 79, 80, 82, 83, 84, 85, 88 and so on showed 100% control against adults of *Tetranychus cinnabarinus*. Compounds 7, 129 and so on showed more than 90% control against adults of *Tetranychus cinnabarinus*.

At the dose of 40 mg/L, compounds 2, 6, 8, 9, 12, 15, 16, 17, 18, 79, 80, 88 and so on showed 100% control against adults of *Tetranychus cinnabarinus*. Compounds 13, 82, 84 and so on showed more than 95% control against adults of *Tetranychus cinnabarinus*.

At the dose of 10 mg/L, compounds 2, 8, 9, 12, 15, 16, 17, 79 and so on showed 100% control against adults of *Tetranychus cinnabarinus*. Compounds 13, 80, 82, 84, 88 and so on showed more than 80% control against adults of *Tetranychus cinnabarinus*.

At the dose of 5 mg/L, compounds 8, 9, 12, 15, 16, 17 and so on showed 100% control against adults of *Tetranychus cinnabarinus*.

At the dose of 0.625 mg/L, compound 15 and so on showed 95% control against adults of *Tetranychus cinnabarinus*. Compounds 8, 9 and so on showed more than 85% control against adults of *Tetranychus cinnabarinus*.

At the dose of 0.31 mg/L, compound 15 and so on showed more than 75% control against adults of *Tetranychus cinnabarinus*.

At the dose of 2.5 mg/L, compounds 9, 15 and so on showed 100% control against nymphs of *Tetranychus cinnabarinus*, compound 8 and so on showed more than 95% control against nymphs of *Tetranychus cinnabarinus*.

At the dose of 0.63 mg/L, compound 15 and so on showed 100% control against nymphs of *Tetranychus cinnabarinus*, compound 9 and so on showed more than 95% control against nymphs of *Tetranychus cinnabarinus*, compound 8 and so on showed more than 75% control against nymphs of *Tetranychus cinnabarinus*.

At the dose of 0.16 mg/L, compounds 9, 15 and so on showed more than 60% control against nymphs of *Tetranychus cinnabarinus*.

At the dose of 10 mg/L, the hatching inhibition rate of compounds 8, 9, 15, 16 against eggs of *Tetranychus cinnabarinus* were 100%.

At the dose of 2.5 mg/L, the hatching inhibition rate of compounds 8, 9, 15, 16 against eggs of *Tetranychus cinnabarinus* were no less than 90%.

The comparative tests of the compounds of the present invention with Compounds 20 (Contrast A), 680 (Contrast B) and 694 (Contrast C) in WO2008145052A1 as contrasts were carried out. The formulas of the three contrasts are as follows:

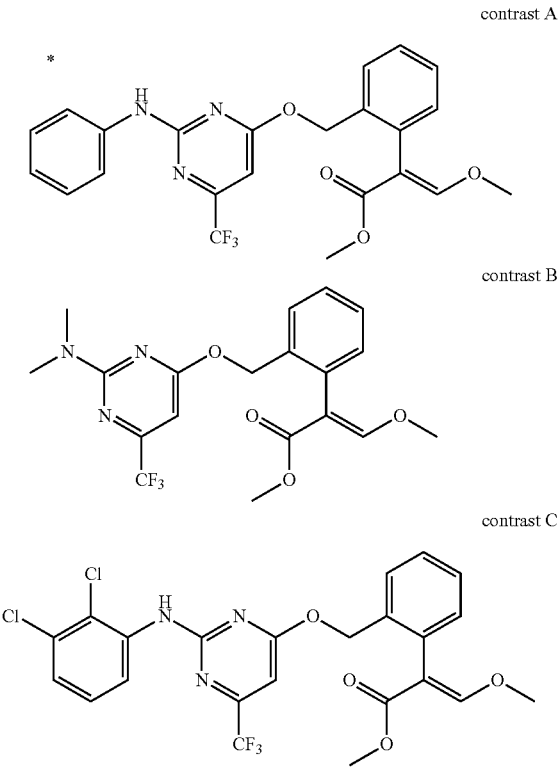

contrast A contrast B contrast C

At the same time, the commercialized products Fluacrypyrim (Titaron, 30% SC, made in Nippon Soda) and Spirodiclofen (Envidor, 24% SC, made in Bayer) were also used as contrasts to carry out the comparative tests compared with the compounds of the present invention.

The test results against adults of *Tetranychus cinnabarinus* were listed in Table 7, the test results against eggs of *Tetranychus cinnabarinus* were listed in Table 8.

TABLE 7

| | mortalities of adults of *Tetranychus cinnabarinus* (%) | | | | | |
|---|---|---|---|---|---|---|
| Compd. | 40 mg/L | 10 mg/L | 5 mg/L | 2.5 mg/L | 1.25 mg/L | 0.625 mg/L |
| Compd. 8 | 100 | 100 | 100 | 100 | 98 | 86 |
| Compd. 9 | 100 | 100 | 100 | 98 | 90 | 88 |
| Compd. 12 | 100 | 100 | 100 | 92 | 86 | 60 |
| Compd. 15 | 100 | 100 | 100 | 100 | 100 | 95 |
| Compd. 16 | 100 | 100 | 100 | 98 | 78 | 60 |
| Compd. 17 | 100 | 100 | 100 | 98 | 70 | 60 |
| Contrast A | 100 | 90 | 60 | 30 | 10 | 0 |
| Contrast B | 0 | 0 | / | / | / | / |
| Fluacrypyrim | 100 | 100 | 95 | 65 | 30 | 0 | note: "/" stands for no data.

TABLE 8

| | hatching inhibition rate against eggs (%) | | |
|---|---|---|---|
| Compd. | 10 mg/L | 2.5 mg/L | 0.625 mg/L |
| Compd. 8 | 100 | 90 | 25 |
| Compd. 9 | 100 | 100 | 20 |
| Contrast A | 100 | 10 | 0 |
| Contrast C | 100 | 10 | 0 |
| Fluacrypyrim | 95 | 10 | 0 |
| Envidor | 100 | 70 | 0 |

Example 7

Field Trial

Field Trial Against Citrus Red Mite (Guilin, China)

The trial was carried out in a 2-year-old Shatang orange orchard in Chaotian town lingchuan county guilin city, trifoliate orange trees were selected as stocks, the intervals between two plants was 1.5×2.5 m, the average height was 1.45 m and the crown width was 1.30 m. Two trees were selected in each plot, with random arrangement and 4 replications. Compound 9 (15% SC) was set at two different doses (100 mg/L and 25 mg/L), and spirodiclofen (24% SC) was set at one dose (48 mg/L). Matabi Supergreen 16 Knapsack Sprayer 16 Liter was used to spray evenly with 2 L of spaying volume for each plant. The plants were treated once on 30 Oct. 2009, at that time, adults, nymphs and eggs of citrus red mite all existed, with adults/eggs=1/1.27. During the day the plants were treated, and the weather was good with the average temperature at 23° C. The first three days after treatment were all clear days. The number of mites was investigated before treatment and on the 1st, 3rd, 10th, 15th, 20th and 30th day after treatment respectively. Two trees of each plot were investigated according to the five directions of the tree crown (east, south, west, north and central), 5 leaves in each direction were investigated to calculate the number of living mites, with 50 leaves each plot. The decline rate of mite population and corrected efficacy were calculated according to formulas below:

The decline rate of mite population(%)=[(the average number of mite on each leaf before treatment−the average number of mite on each leaf after treatment)/the average number of mite on each leaf before treatment]×100.

Corrected efficacy(%)=[(the decline rate of mite population in treated area−the decline rate of mite population in untreated area)/(100−the decline rate of mite population in untreated area)]×100.

The trial results in field plot of compound 9 against citrus red mite (Guilin Guangxi) were listed in Table 9:

TABLE 9

| Compd. | mg/L | Corrected efficacy (%) | | | | | |
|---|---|---|---|---|---|---|---|
| | | the 1st day after treatment | the 3rd day after treatment | the 10th day after treatment | the 15th day after treatment | the 20th day after treatment | the 30th day after treatment |
| Compd. 9 | 100 | 92 | 96 | 96 | 95 | 97 | 94 |
| | 25 | 90 | 92 | 83 | 91 | 92 | 91 |
| Spirodiclofen | 48 | 59 | 72 | 75 | 76 | 83 | 82 |

We claim:

1. An E-type phenyl acrylic ester compound containing a substituted anilino pyrimidine group having the general formula I:

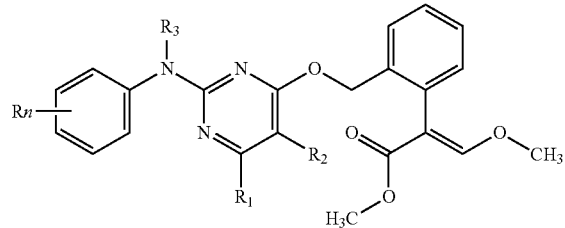

I wherein:

$R_1$ is $CCl_3$, $CF_2Cl$, $CFCl_2$, $CF_3$, or $CH_2CF_3$;

$R_2$ is H, Cl, or $CH_3$;

$R_3$ is H, $C_1$-$C_4$alkyl, alkylsulfonyl, or $C_1$-$C_4$alkylcarbonyl;

Rn is selected from the group consisting of 2,4-difluoro, 2,4-dichloro, 2-fluoro-4-chloro, 2-chloro-4-fluoro, 2,3,4-trifluoro, 2,3,4-trichloro, 2,4-difluoro-3-methyl, 2,4-dichloro-3-methyl, 2-fluoro-3,4-dichloro, and 2-chloro-3,4-difluoro;

or a hydrochloride, phosphate, acetate, benzene sulfonate, or oxalate salt thereof.

2. The compound according to claim 1, wherein $R_1$ is $CF_3$;

$R_3$ is H; and

Rn is selected from the group consisting of 2,4-difluoro, 2,4-dichloro, 2-fluoro-4-chloro, 2-chloro-4-fluoro, 2,3,4-trifluoro, 2,3,4-trichloro, and 2,4-dichloro-3-methyl.

3. A method for controlling harmful insects and mites in agricultural and other fields which comprises contacting the insects and mites with the compound of claim 1.

4. A composition of insecticides and/or acaricides, comprising the compound of claim 1 as an active ingredient and acceptable carrier in agriculture, wherein the weight percentage of the active ingredient in the composition is 0.5-90%.

5. A method for controlling harmful insects and mites in agricultural and other fields which comprises contacting the insects and mites with the composition of claim 4.

* * * * *